United States Patent
Brauer et al.

(10) Patent No.: US 7,125,393 B2
(45) Date of Patent: Oct. 24, 2006

(54) DEVICE FOR CARRYING FLUIDS FOR A MEDICAL TREATMENT DEVICE

(75) Inventors: Helge Brauer, Gochsheim (DE); Walter Ehrenberger, Gerolzhofen (DE); Helmuth Ender, Zeil (DE); Joachim Noack, Bad Neustadt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 462 days.

(21) Appl. No.: 10/644,746

(22) Filed: Aug. 21, 2003

(65) Prior Publication Data

US 2004/0040620 A1    Mar. 4, 2004

(30) Foreign Application Priority Data

Aug. 28, 2002    (DE)    ................. 102 39 598

(51) Int. Cl.
  *A61M 37/00*    (2006.01)
  *B01D 11/00*    (2006.01)
  *B01D 35/00*    (2006.01)
  *B01D 21/24*    (2006.01)
  *C02F 1/44*    (2006.01)

(52) U.S. Cl. .................... 604/4.01; 604/5.01; 210/647; 210/739; 210/744; 210/85; 210/87; 210/97; 210/321.71; 210/321.72

(58) Field of Classification Search ...... 604/4.01–5.04, 604/6.09, 6.1, 6.11, 6.16; 210/645–647, 210/650–651, 739–746, 767, 97, 85–90, 210/101, 103–104, 143, 198.1, 321.6, 321.71–321.72, 210/902–905
See application file for complete search history.

(56) References Cited

U.S. PATENT DOCUMENTS

| | | | |
|---|---|---|---|
| 4,267,040 A | 5/1981 | Schäl | 210/104 |
| 4,366,061 A * | 12/1982 | Papanek et al. | 210/647 |
| 4,431,425 A | 2/1984 | Thompson et al. | 604/246 |
| 5,580,460 A | 12/1996 | Polaschegg | 210/646 |

FOREIGN PATENT DOCUMENTS

| | | |
|---|---|---|
| DE | 26 34 238 | 2/1978 |
| DE | 30 16 720 | 11/1981 |
| DE | 28 38 414 | 10/1984 |
| DE | 197 28 800 | 2/1999 |
| EP | 0 306 241 | 3/1989 |

* cited by examiner

*Primary Examiner*—Patricia Bianco
(74) *Attorney, Agent, or Firm*—Jacobson Holman PLLC

(57) ABSTRACT

A device for carrying fluids for a medical treatment device with two balancing chambers, each having two partial chambers. The filling times of the partial chambers are initially determined using a monitoring device, and then the filling times of the first partial chambers of the first and second balancing chambers, are compared to the filling times of the second partial chambers of the first and second balancing chambers, respectively, to detect leakage or an incomplete filling or discharging of the respective partial chambers.

13 Claims, 1 Drawing Sheet

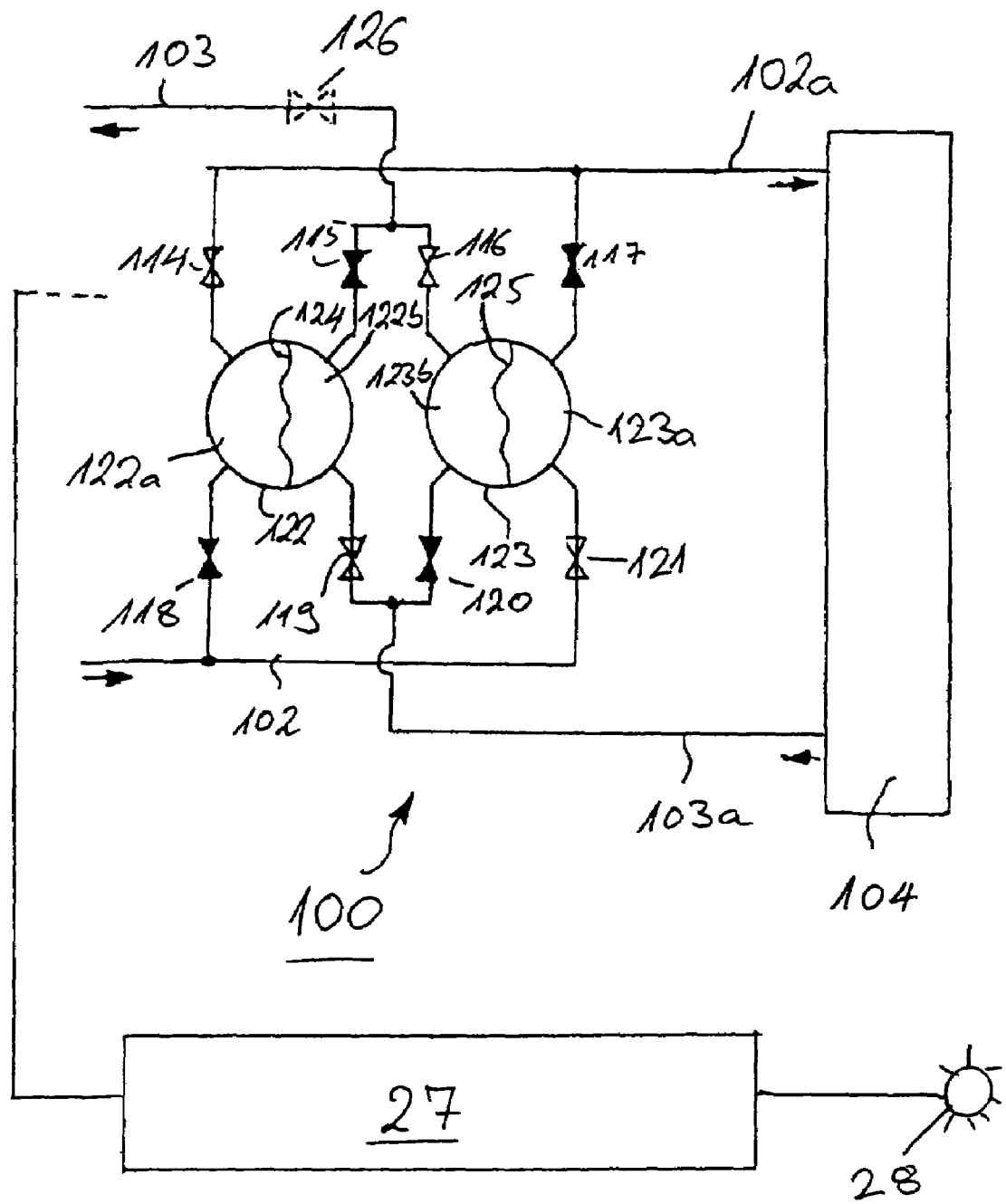
Fig.

DEVICE FOR CARRYING FLUIDS FOR A MEDICAL TREATMENT DEVICE

BACKGROUND OF THE INVENTION

1. Field of the Invention

The invention relates to a device for carrying fluids for a medical treatment device with two balancing chambers of equal volume which are each separated into a first and a second partial chamber by means of a flexible separating wall. Each of the first partial chambers has at least one first supply line and at least one first discharge line, and each of the second partial chambers has at least a second supply line and at least a second discharge line, as well as an analysis device.

2. Description of the Related Art

In order to remove substances usually eliminated with urine, and for the removal of fluids, several different processes are used with acute and chronic kidney failure for the surgical purification of blood, or treatment of blood, respectively. In hemodialysis (HD), diffuse translocation prevails, while convective translocation via a membrane is available in the case of hemofiltration (HF). A combination of both processes results in hemodiafiltration (HDF). In peritoneal dialysis (PD) peritoneum is utilized as the contact membrane.

Due to the large exchange quantities, the necessity of an exact balancing process of the fluids removed from the patient and the fluids recirculated to the patient during the entire treatment period exists with the said process.

A hemodiafiltration device with volumetric balancing is known, for instance, from DE 26 34 238 A1. The balancing device of the known hemodiafiltration device has a volume-rigid hollow body, which is separated into two chambers by means of a flexible separating wall. Each chamber has an input and outlet, on which supply and discharge lines for fresh or used dialyzing fluids are arranged, whereby a shut-off valve is switched in each line. Furthermore, pumps are provided for carrying the fresh and used dialyzing fluid, as well as a control unit, which allow the alternating filling of the two chambers. A pressure gauge device is each arranged in the input line of the first and second chambers, which monitors the pressure in the line. Once a chamber is filled, a pressure increase occurs, which switches the respective pump off.

U.S. Pat. No. 4,431,425 A describes a device for the detection of the position of the flexible separating wall of a balancing device with an optical detector, which is arranged on the exterior of the balancing chamber. The known device is of disadvantage insofar as the housing of the balancing chamber must consist of a transparent material.

A device for carrying fluids for a medical treatment device is known from DE 197 28 800 C1, in which pressure impulses are received per time units in a balancing chamber. In this way, the frequency of balancing chamber strokes can be determined per time unit. This represents the monitoring process of the complete filling and draining of the balancing chamber.

A balancing chamber system is also known from DE 28 38 414 C2, according to which any leak possibly occurring in the membrane-like separating wall of the respective carrying chamber, or the balancing chamber, respectively, can be detected by means of a conductivity monitoring system. Such a leak is undesired, as it leads to the mixing of fresh and used dialyzing fluids, which particularly results in a change in treatment effectiveness.

Additionally, the filling condition of the balancing chamber is difficult to detect, because the pressure increase at the end of the circulation cycle is not very distinct. The leak detection by means of a conductivity monitoring system, however, is not capable of functioning precisely, because the conductivity of the mixed fluids hardly differs from each other. Particularly small leaks can practically not be detected at all.

SUMMARY OF THE INVENTION

It is therefore the task of the invention to further develop a generic device for carrying fluids for a medical treatment in such a way that any leaks possibly occurring in the membrane-like separating wall can be safely detected.

According to the invention, this task is solved by a device for carrying fluids for a medical treatment device with two balancing chambers of equal volume which are each separated into a first and a second partial chamber by means of a flexible separating wall, each of the first partial chambers having at least one first supply line and at least one first discharge line, and each of the second partial chambers having at least a second supply line and at least a second discharge line. The filling times of the partial chambers are initially determined in a generic device for carrying fluids for a medical treatment device by means of an analysis device, and then the filling times of the respective first partial chambers and of the first and second balancing chambers, and/or of the second partial chambers of the first and second balancing chambers are compared to each other. The present invention is based on the knowledge that the filling times for filling of the partial chamber volume are constant at a predetermined flow rate. Should a difference of filling times of the parallel connected first partial chambers of the balancing chambers, or of the second partial chambers of the balancing chambers occur, this would be an indication of a leak in the flexible separating wall.

For example, the filling times could be stored in memory as comparison values for each actually measured filling times. In case of a deviation of the filling times by a predetermined value of $\Delta T$, the analysis device can draw a conclusion on a respective leak in the separating wall.

According to a preferred embodiment alternative of the invention, an optic and/or acoustic signal generator is additionally included in the device, via which an alarm signal can be generated in case a leak was detected in the flexible separating wall.

Finally, the leak detection signal can be generated again only if the predetermined time difference is exceeded several times according to predetermined criteria. This safely prevents any false alarms.

A comparison between the filling times of each partial chamber of the first balancing chamber is now performed with each one of the respective partial chambers of the second balancing chamber by means of the device according to the invention. This compensates any influences caused by flow pumps, flow profiles, etc. Therefore, the storage of respective calibrating times into the memory of the analysis device is conveniently not necessary.

BRIEF DESCRIPTION OF THE DRAWING

Additional details and benefits of the invention are explained in more detail by means of an embodiment example illustrated in the drawing. It shows in the only FIGURE a simplified principle diagram of an embodiment example of the device according to the invention.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The FIGURE also shows the course of the dialyzing fluid 100 of a hemodialysis device according to the invention with volumetric balancing in a strongly simplified illustration. The balancing device consists of the balancing chambers 122 and 123 and the associated valves 114 to 121. Integral parts of the balancing device are the two chambers 122 and 123. According to the principle, they consist of volume-rigid hollow bodies with two chambers each, which are separated from each other by means of a flexible, tightly closing element 124 or 125 so that if one of the chambers is increased, the other chamber is inevitably decreased by an equal amount. In a schematic illustration of the FIGURE, the chambers 122 and 123, for instance, are illustrated as balls, and the flexible elements 124 and 125 are illustrated as a membrane. With regard to the dosage function it is additionally important for the actual construction of the chambers and the flexible elements within the said chambers; that the displacement of the flexible elements from one extreme position to the other leads to a reproducible volume displacement. For example, in the embodiment indicated in the FIGURE, this is achieved in that the membranes 124 and 125 completely abut against the right or left wall of the respective chamber in their extreme positions so that a volume displacement in the amount of the entire chamber volume occurs with the movement from one extreme position to the other.

Valves 114 to 121 associated with the balancing chambers form two groups that are operated alternatively. When the valves of group A (115, 117, 118, 120) are open, the valves of group B (114, 116, 119, 121) are closed, and vice versa. The two chambers therefore operate in an alternating fashion, periodically exchanging their functions. While one of the two chambers each is integrated into the circulation (102a, 103a) of the dialyzer 104, the other chamber is charged with new dialyzing fluid via the supply line 102, and the used dialyzing fluid is displaced into the discharge line 103 simultaneously.

When the valves of group A (illustrated in dark) are open, and the valves of group B (illustrated light) are closed, the chamber 122 is charged with fresh dialyzing fluid, while the chamber 123 serves for feeding the dialyzer. The charging process of chamber 122 results from the fact that fresh fluid flows under pressure from the opened valve 118 into the chamber 122a so that the membrane 124 dodges the same, and the dialyzing fluid located in the chamber 122b beyond the membrane is displaced through the open valve 115 into the terminal line 103. Once the membrane has connected completely to the right chamber wall, this charging process is completed.

Meanwhile the dialyzer is fed from the chamber 123 in that the fresh dialyzing fluid located in cavity 123a is fed through the opened valve 117 to the dialyzer via the line 102a, and is recirculated as used dialyzing fluid from the dialyzer via the line 103a and the open valve 120 into the cavity 123b of the same chamber. Due to the volume rigidity of the balancing chamber, the recirculated amount of fluid must exactly match the amount of fluid fed to the dialyzer. The dialyzing fluid flows into a quasi closed circuit, because the beginning and the end are connected to each other via the displaceable element in the balancing chamber. Any mixing of fresh and used dialyzing fluid does not occur, however. As soon as the membrane in the chamber 123 has connected to the right chamber wall completely, the process is completed. In order to continue to maintain the flow through the dialyzer 104, only the valves are switched so that the two chambers 122 and 123 of the balancing device exchange their functions.

If the valves of the group A are closed, and the valves of group B are open, fresh dialyzing fluid can continue to flow through the opened valve 114 from the cavity 122a of the chamber 122, while the equal amount of used dialyzing fluid is fed from the dialyzer into the cavity 122b on the other side of the membrane via the open valve 119. At the beginning of this process, the cavity 122a is at a maximum, and the cavity 122b is at a minimum filling state, because the cavity 122a, as described, has been completely filled with fresh dialyzing fluid during the previous process step. While the dialyzer is fed from the chamber 122, chamber 123, the cavity 123b of which is completely filled with used dialyzing fluid in the previous process step, is charged with fresh dialyzing fluid. The fresh dialyzing fluid flows into the cavity 123a via the open valve 121, and the used dialyzing fluid present in the cavity 123b is displaced into the discharge line 103 via the open valve 116.

However, the switchover of the valve groups must occur at the time when the supply of the balancing chamber, from which the dialyzer 104 is currently being fed, is depleted. The charging of the other balancing chamber should be completed at this time, which can be achieved without any problems by means of a respectively high charging speed. The signal for the switchover of the valves can be obtained in different ways. Since the dialyzing fluid flow stops in the dialyzer circulation as soon as the membrane has reached its extreme position in the balancing chamber feeding the dialyzer 104, a flow control unit with a device for signal triggering, for example, could be utilized for this purpose in case the flow falls below the minimum value. Another possibility is to utilize a pressure modification that is contingent on the reaching of the end position in order to trigger the switchover function. Yet another possibility is to utilize the increased power consumption of the charging pump at the end of the filling cycle for the detection of the final position.

In order to detect an incomplete filling or discharging of the respective partial chambers 122a or 122b, and 123a or 123b of the balancing chambers 122 and 123, a monitoring device 27 is provided, which includes a pressure gauge device that is arranged on the exterior of the balancing chambers, as well as an analysis device and a processing device. The monitoring device is illustrated in the FIGURE only very schematically for reasons of simplification, i.e. without the arrangement of the individual pressure gauge devices, as well as of the respective connection lines. The pressure gauge devices must each be connected at least either to the first partial chambers 122a and 123a, or to the second partial chambers 122b and 123b, which may also occur via the supply or discharge lines.

The filling times of the partial chambers 122a and 123a, or 122b and 123b are now determined by means of the monitoring device 27. In case of a deviation of filling times for the respective partial chambers 122a or 123a to be filled on one hand, and 122b or 123b on the other hand, a leak detection signal is released by a time interval ΔT, by means of which an optical signal generator 28 can be activated.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A device for carrying fluids for a medical treatment device comprising:
   two balancing chambers of equal volume, each of said balancing chambers being separated into a first partial chamber and a second partial chamber by a flexible separating wall;
   each of said first partial chambers having at least one first supply line and at least one first discharge line, and each of said second partial chambers having at least a second supply line and at least a second discharge line; and
   a monitoring device configured to initially determine filling times of the first partial chambers or of the second partial chambers or both, and to compare the filling times so determined to detect a filling time difference indicating leakage or an incomplete filling or discharging of the respective partial chambers.

2. The device according to claim 1, wherein a leak detection signal is released if a predetermined time difference (ΔT) is exceeded.

3. The device according to claim 2, wherein said leak detection signal is generated by an optical and/or acoustical signal generator.

4. The device according to claim 2, wherein the leak detection signal cannot be released until the predetermined time difference (ΔT) is exceeded several times according to predetermined criteria.

5. The device according to claim 1, wherein each of said balancing chambers has a rigid volume.

6. The device according to claim 1, wherein for a respective balancing chamber, a volume of said first partial chamber when completely filled is the same as a volume of said second partial chamber when completely filled.

7. The device according to claim 1, wherein within each of said balancing chambers, said flexible separating wall is movable from a first extreme position completely abutting against a left wall of said balancing chamber to a second extreme position completely abutting against a right wall of said balancing chamber so that a volume displacement in an amount corresponding to an entire chamber volume occurs with the movement between the first and second extreme positions.

8. A device for carrying fluids for a medical treatment device comprising:
   two balancing chambers of equal volume, each of said balancing chambers being separated into a first partial chamber and a second partial chamber by a flexible separating wall, a volume of each of said first and second partial chambers when completely filled being the same;
   each of said first and second partial chambers having a respective supply line and a respective discharge line controllable by valves so that, for each balancing chamber, as the respective first partial chamber is filled the respective second partial chamber is discharged; and
   a monitoring device configured to initially determine filling times of the first partial chambers or of the second partial chambers or both, and to compare the filling times so determined to detect a time difference indicating leakage or an incomplete filling or discharging of the respective partial chambers.

9. The device according to claim 8, wherein a leak detection signal is released if a predetermined time difference (ΔT) is exceeded.

10. The device according to claim 9, wherein said leak detection signal is generated by an optical and/or acoustical signal generator.

11. The device according to claim 9, wherein the leak detection signal cannot be released until the predetermined time difference (ΔT) is exceeded several times according to predetermined criteria.

12. The device according to claim 8, wherein each of said balancing chambers has a rigid volume.

13. The device according to claim 8, wherein within each of said balancing chambers, said flexible separating wall is movable from a first extreme position completely abutting against a left wall of said balancing chamber to a second extreme position completely abutting against a right wall of said balancing chamber so that a volume displacement in an amount corresponding to an entire chamber volume occurs with the movement between the first and second extreme positions.

* * * * *